US009155556B2

(12) United States Patent
Fuerst et al.

(10) Patent No.: US 9,155,556 B2
(45) Date of Patent: Oct. 13, 2015

(54) SUPPORT ELEMENT FOR CIRCUMCISION AND SYSTEM COMPRISING THE SAME

(71) Applicant: Circ MedTech Ltd., Road Town (VG)

(72) Inventors: Oren Fuerst, Ramat Hasharon (IL); Ido Kilemnick, Herzliya (IL); Shaul Shohat, Kfar Haoranim (IL)

(73) Assignee: Circ Med Tech Ltd., Road Town, Tortola (VG)

( * ) Notice: Subject to any disclaimer, the term of this patent is extended or adjusted under 35 U.S.C. 154(b) by 0 days.

(21) Appl. No.: 14/313,187

(22) Filed: Jun. 24, 2014

(65) Prior Publication Data

US 2014/0309654 A1    Oct. 16, 2014

Related U.S. Application Data

(63) Continuation of application No. 13/991,760, filed as application No. PCT/IL2011/050040 on Dec. 5, 2011.

(60) Provisional application No. 61/419,903, filed on Dec. 6, 2010.

(51) Int. Cl.
*A61B 17/326* (2006.01)
*A61B 19/00* (2006.01)

(52) U.S. Cl.
CPC ......... *A61B 17/326* (2013.01); *A61B 2019/461* (2013.01)

(58) Field of Classification Search
CPC .............. A61B 17/326; A61B 17/0487; A61B 17/122; A61B 17/1227; A61B 17/128; A61B 17/1285; A61B 17/083; A61B 17/11; A61B 17/12; F16L 17/06; B25B 7/126; B25B 7/12; B25B 27/205
USPC ................. 606/118; 29/229; 81/301
See application file for complete search history.

(56) References Cited

U.S. PATENT DOCUMENTS 2,294,852 A  *  9/1942  Smith ........................... 606/118
2,453,056 A  *  11/1948  Zack ............................. 606/153
(Continued)

FOREIGN PATENT DOCUMENTS

CN          2031271        1/1989
CN          2048737        12/1989
(Continued)

OTHER PUBLICATIONS

Cir-Ring International, male circumcision—Circ Ring; http://www.circ-ring.de/us/circringenglish.html (owned by the company Circ-Ring International and known commercially as the Zhenxi Ring) (2006).

(Continued)

*Primary Examiner* — Dianne Dornbusch
(74) *Attorney, Agent, or Firm* — Greenberg Traurig, LLP

(57) ABSTRACT

The present disclosure provides a support element (110) for use in effecting ischemic necrosis in a foreskin of a penis, being a closed-loop member defining an opening dimensioned to permit a penis glans to pass therethrough and having an inner surface and an outer surface; the outer surface comprising a circumferential support (118) for an elastic ring (150) to be mounted thereon, said circumferential support being formed within a groove (120) in at least part of the outer surface; at least one first segment of the outer surface having an outer curvature of a radius larger than that of its flanking second segments. Also provided herein is a system (100) for effecting ischemic necrosis in a foreskin of a penis, comprising the support element (110) and elastic ring (150), and optionally a deployment element (160) for mounting the elastic ring over the foreskin and support element.

13 Claims, 11 Drawing Sheets

(56) References Cited

U.S. PATENT DOCUMENTS

| | | | |
|---|---|---|---|
| 2,538,136 A * | 1/1951 | Twachtman | 602/1 |
| 2,544,037 A * | 3/1951 | Moseley | 606/118 |
| 2,561,176 A * | 7/1951 | Buckingham | 606/118 |
| 2,695,616 A | 11/1954 | Hansell | |
| 2,741,829 A * | 4/1956 | Krodel | 29/229 |
| 2,961,755 A * | 11/1960 | Prince | 29/235 |
| 3,052,970 A * | 9/1962 | Perrin | 29/229 |
| 3,319,325 A * | 5/1967 | Nessamar et al. | 29/235 |
| 3,347,083 A * | 10/1967 | Turpin et al. | 72/393 |
| 3,604,096 A * | 9/1971 | Shiroma | 29/235 |
| 3,683,926 A * | 8/1972 | Suzuki | 606/154 |
| 4,203,191 A * | 5/1980 | Gibson, Sr. | 29/451 |
| 4,368,736 A * | 1/1983 | Kaster | 606/153 |
| 4,381,767 A * | 5/1983 | Finney | 600/40 |
| 4,387,705 A * | 6/1983 | Finney | 600/30 |
| 4,491,136 A * | 1/1985 | LeVeen | 606/118 |
| 4,657,019 A * | 4/1987 | Walsh et al. | 606/153 |
| 4,843,668 A * | 7/1989 | Bondar | 7/164 |
| 4,917,087 A * | 4/1990 | Walsh et al. | 606/153 |
| 5,269,788 A * | 12/1993 | Nelson, III | 606/118 |
| 5,282,795 A * | 2/1994 | Finney | 604/351 |
| D355,708 S * | 2/1995 | Caine | D23/260 |
| 5,649,933 A * | 7/1997 | Singh | 606/118 |
| 5,860,988 A * | 1/1999 | Rawlings | 606/118 |
| 6,722,011 B1 * | 4/2004 | Bacon | 29/451 |
| 6,929,648 B2 * | 8/2005 | Richard et al. | 606/153 |
| 6,993,816 B2 * | 2/2006 | Greenhill | 29/229 |
| D558,310 S * | 12/2007 | Quesada | D23/269 |
| D574,934 S * | 8/2008 | Darce et al. | D23/269 |
| D670,807 S * | 11/2012 | Fuerst | D24/143 |
| 8,366,651 B2 * | 2/2013 | Dakin et al. | 604/8 |
| 8,512,361 B2 * | 8/2013 | Gronberg et al. | 606/153 |
| 2007/0013146 A1 * | 1/2007 | Gariepy | 277/608 |
| 2007/0204451 A1 * | 9/2007 | Fistor | 29/229 |
| 2008/0154283 A1 * | 6/2008 | Shang | 606/118 |
| 2009/0138030 A1 * | 5/2009 | Gronberg | 606/153 |
| 2011/0098718 A1 * | 4/2011 | Shang | 606/118 |
| 2012/0203242 A1 * | 8/2012 | Fuerst et al. | 606/118 |

FOREIGN PATENT DOCUMENTS

| | | |
|---|---|---|
| CN | 2256299 | 6/1997 |
| CN | 2395698 | 9/2000 |
| CN | 2403373 | 11/2000 |
| CN | 2894623 | 5/2007 |
| CN | 201127640 | 10/2008 |
| CN | 101301219 | 11/2008 |
| WO | 2005039424 A1 | 6/2005 |

OTHER PUBLICATIONS

PCT International Search Report dated May 29, 2012 issued in PCT/IL2011/050040 (6 Pages).

* cited by examiner

SUPPORT ELEMENT FOR CIRCUMCISION AND SYSTEM COMPRISING THE SAME

RELATED APPLICATIONS

This application is a continuation of U.S. patent application Ser. No. 13/991,760, filed on Aug. 19, 2013, which is a national phase filing under 35 U.S.C. 371 of PCT International Application No. PCT/IL2011/050040, filed on Dec. 5, 2011, which claims the benefit of U.S. Provisional Application No. 61/419,903 filed on Dec. 6, 2010, the entirety of these applications is hereby incorporated herein by reference for the teachings therein.

FIELD OF THE INVENTION

This invention relates to non-surgical circumcision and to elements and system used for performing the same.

BACKGROUND OF THE INVENTION

Male circumcision is one of the most common surgical procedures in the world and is performed for ritualistic as well as hygienic and disease prevention reasons. Approximately a third of human males worldwide receive a circumcision at some point in their lives. Circumcision has traditionally been performed either immediately after birth, during childhood, during adolescence or occasionally on young adults (i.e., after the teenage years).

One conventional method for performing circumcision is by surgically removing the foreskin after physically pulling the foreskin over the glans. In such methods, the foreskin is removed while it is still a live tissue, usually causing bleeding. Such methods may involve hemorrhaging and a relatively long period of healing of the incision (e.g., up to a few weeks), while inducing pain in an individual. When such a procedure is performed on adult males, suturing is required. In general, such methods are recognized as not being scalable for mass circumcision campaigns, in particular in areas where medical facilities may be sparse or not available and where skilled personnel is scarce. It is therefore desirable to have a circumcision device that is scalable for mass circumcision in that it is a fast procedure, requires no sterile settings, and can easily be administered by low cadre professionals such as nurses, and is also associated with as little pain as possible to increase acceptability and satisfaction of the procedure, leading to more men agreeing to undergo the procedure.

Other methods and devices for performing circumcision are known in the art, some use a device in the form of a ring enclosing onto the foreskin. One such device is shown on the website http://www.circ-ring.de/us/circ ring english.html (owned by the company Circ-Ring International and known commercially as the Zhenxi Ring). The use of this device requires anesthesia.

U.S. Pat. No. 5,269,788 issued to Nelson, III, and entitled "Adjustable Hemostatic Circumcision Dressing and Method of its Use," is directed to a device for performing circumcision and describes a circumcision dressing, which comprises an inner ring that is discontinuous and is positioned between the prepuce and shaft of the penis and an outer ring.

US patent publication No. 2,561,176 issued to Buckingham Charles T describes a one piece compression clamp that is left on the prepuce for a few days after the circumcision.

U.S. Pat. No. 2,544,037 issued To Moseley Mortimer H describes a surgical instrument comprising a guard positioned between the prepuce and the shaft and a clamp positioned in encompassing position about the prepuce crushing the prepuce against the guard to cause hemostasis.

International patent application publication No. WO2005/039424 describes a circumcision apparatus composed of three components, glans loop, a rubber ring and a clamping mechanism, the rubber ring being placed between the glans loop and the clamping mechanism.

Chinese publication CN2256299 describes it its abstract a ring cutter comprising a ring loop, having a ring groove present on the outer circle of this ring loop, and a flexible loop which is stretched onto the ring groove of the ring loop. The ring loop and the flexible rubber loop form a ring bracket, which is inserted and supported in the prepuce, thereby blocking the blood circulation of the front part of the prepuce so that the prepuce falls off.

Chinese publication CN2403373 describes in its abstract a circumcision apparatus used for prepuce excision comprises a ring support arranged on the inner side of prepuce and an elastic excision ring arranged on the outside of the prepuce, with both being mutually acted, allowing the blood transmission of the prepuce to be cut off, and prepuce tissues are necrotized to fall off.

Chinese publication CN2031271 describes a circumcision apparatus composed of an inner ring and an outer elastic ring.

SUMMARY OF THE INVENTION

The present disclosure provides, in accordance with a first of its aspects, a support element for use in effecting ischemic necrosis in a foreskin of a penis, being a closed-loop member defining an opening dimensioned to permit a penis glans to pass therethrough and having an inner surface and an outer surface; the outer surface comprising a circumferential support for an elastic ring to be mounted thereon, said circumferential support being formed within a groove in at least part of the outer surface; at least one first segment of the outer surface having an outer curvature of a radius larger than that of its flanking second segments.

In accordance with a second aspect, the present disclosure provides a system for effecting ischemic necrosis in a foreskin of a penis, comprising: an elastic ring; and a support element defining a closed loop defining an opening dimensioned to permit a penis to pass therethrough and having an inner surface and an outer surface; the outer surface comprising a circumferential support for the elastic ring to be mounted thereon, said support being formed within a groove in at least part of the outer surface; at least one segment of the outer surface having a curvature of a radius larger than that of its flanking segments.

In one embodiment, the system of the invention comprises a deployment element having an arrangement of holders for holding the elastic ring in a stretched state thereof and for mounting the elastic ring within the circumferential support of said support element.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF SOME NON-LIMITING EMBODIMENTS

The present invention provides a support element and a system for non-surgical circumcision and in particular for use in effecting ischemic necrosis in a foreskin of a penis and removal of the necrotic foreskin thereafter. As will be appreciated from the description below, the support element, the system and the method of using the same may be applicable for any male subject, including infants, children, adolescents and adults.

The support element according to the invention is a closed-loop member with an opening dimensioned to permit a penis glans to pass therethrough and having an inner surface and an outer surface; the outer surface comprising a circumferential support for an elastic ring to be mounted thereon, said circumferential support being formed within a groove in at least part of the outer surface; at least one first segment of the outer surface having an outer curvature of a radius larger than that of its flanking second segments.

Figure 1A:
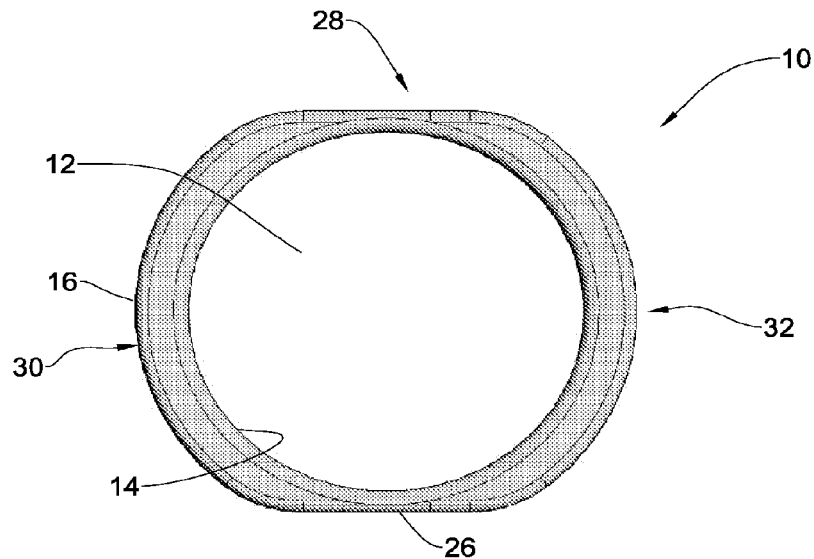
FIGS. 1A and 1B show a side view and perspective view, respectively, of a support element constructed and operable in accordance with an embodiment of the invention.
Figure 1B:
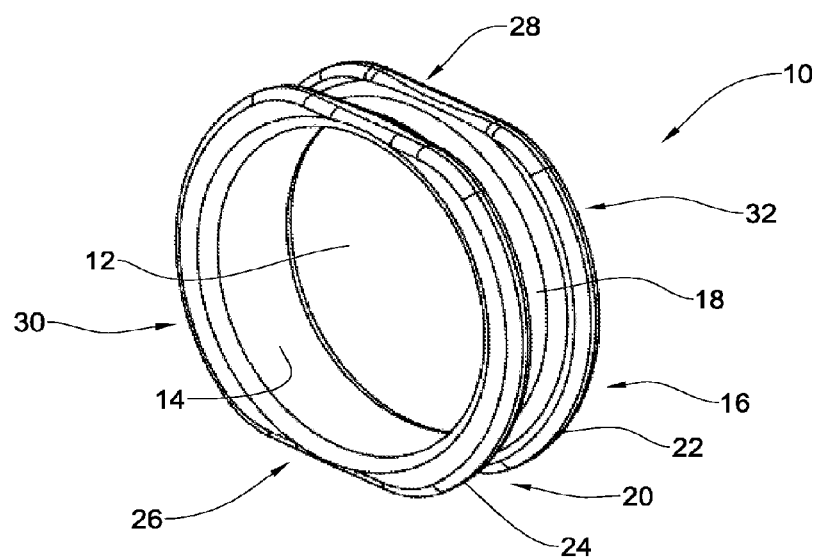

Referring first to FIGS. 1A and 1B, there is provided a support element 10, being a closed loop member and having an opening 12, which is dimensioned such, as is also illustrated below, for the penis glans to pass therethrough. Element 10 has an inner surface 14 which, in this specific embodiment, has a generally circular contour; and an outer surface 16 comprising a circumferential support 18, configured to receive and hold an elastic ring (not illustrated). Further, circumferential support 18 is formed within a groove 20, defined by flanking side walls 22, 24, the top of the side walls defining an outer curvature.

According to this particular and preferred embodiment support element 10 is formed with two opposite first segments 26 and 28 where the outer curvature has a radius larger than that of the two flanking oppositely arranged second segments 30, 32. In this particular embodiment, the outer curvature of the two opposite first segments 26 and 28 is zero (are flat). However, it is to be appreciated that the outer curvature of such first segment may be greater than zero, as long as it is larger than the outer curvature of its flanking segments.

While FIGS. 1A and 1B illustrate a support element with one such first segment, it is to be appreciated that the support element according to the invention may comprise a single such first segment as well as two or more such first segments. Nonetheless, it is noted that a preferred embodiment of the invention comprise two opposite (parallel) first segments, having zero curvature at their outer surface (i.e. essentially flat outer surfaces).

The support element according to the invention and as exemplified in FIGS. 1A and 1B is typically made of a rigid material. When referring to rigid material it is to be understood as any material that substantially retains is shape once an elastic ring is mounted thereon. The rigid material may be of any non-resilient (non-elastic) material, such as, without being limited thereto, plastic such as polycarbonate, polyoxymethylene such as Delrin® (DuPont) acetal resin, polyether ether ketone (PEEK), but also, of a resilient material, having, however, lower elasticity than that of the elastic ring to be mounted thereon. In this context, a resilient material, or elastic material, are to be understood as meaning a material that is capable of regaining its original shape or position after bending, stretching, compression, or other deformation. The resilient material is also one that would conform to the counter of the circumferential support which it overlays but will exert a pronounced pressure on the support because of its tendency to return to its original shape.

Figure 2:
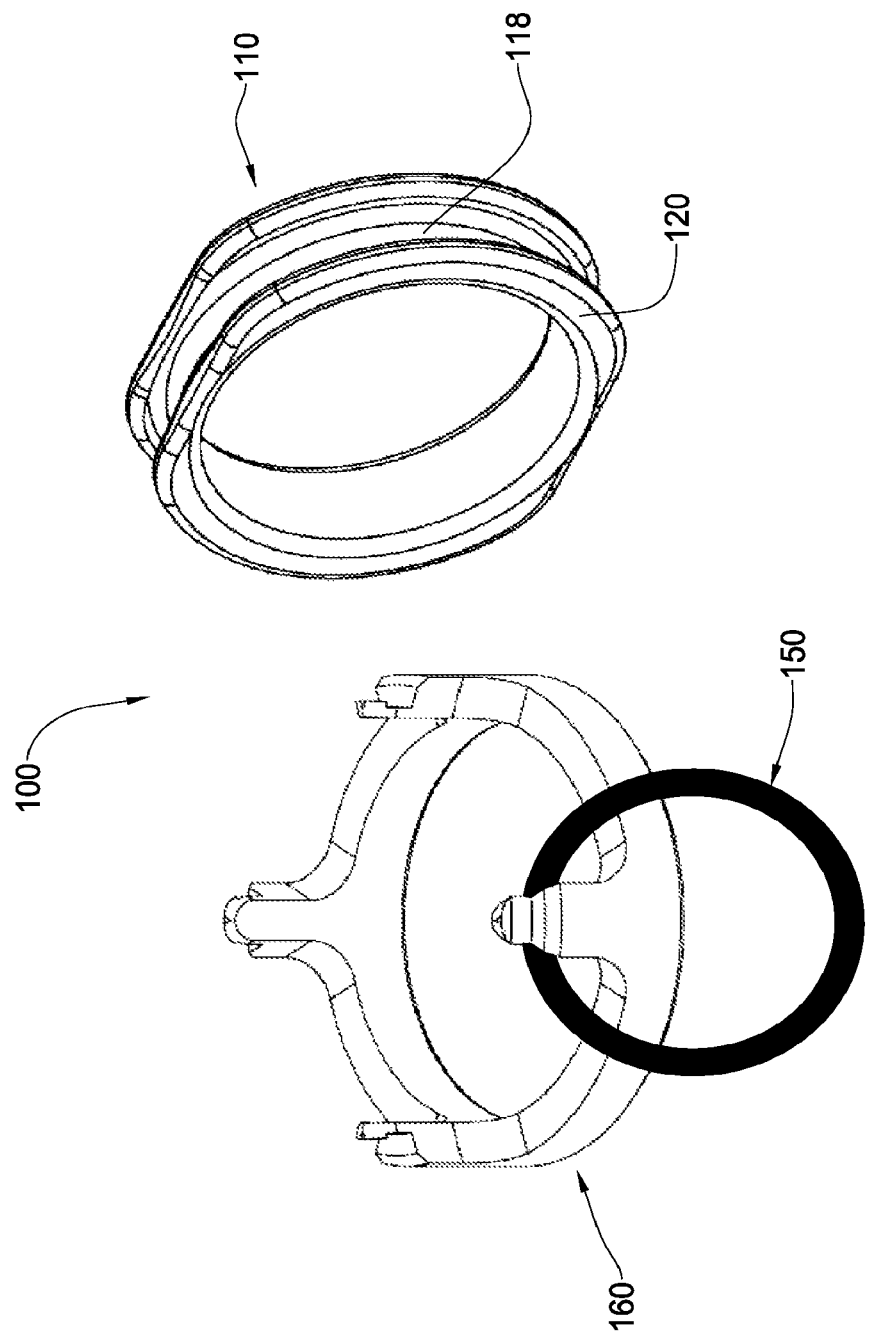
FIG. 2 shows a perspective view of a system constructed and operable in accordance with an embodiment of the invention.

The invention also provides a system for effecting ischemic necrosis in a foreskin of a penis. Reference is now made to FIG. 2 showing a system according an embodiment of the invention. For simplicity, like reference numerals to those used in FIG. 1A or 1B, shifted by 100, are used in FIG. 2 to identify components having a same or similar function. For example, support element 10 in FIG. 1A is has the same function as support element 110 in FIG. 2

A system 100, as shown in FIG. 2, comprises a support element 110, an elastic ring 150 to be stretched over circumferential support 118 and placed in its groove 120. According to the embodiment of FIG. 2, the system may also comprise a deployment element 160.

Elastic ring is made of an elastic material, and is shown in this embodiment to be made of rubber, such as ethylene propylene diene monomer (EPDM) rubber, polyurethane rubber or silicone rubber. However, it is to be appreciated that the elastic ring may be of any elastic or elastomeric material, other than rubber, such as a spring or spring-like material such as nitinol, steel springs.

Elastic ring may be secured with a safety thread. The safety thread may be a loop closed onto the elastic ring and may be used to lift the elastic ring, e.g. in case the elastic ring is misplaced and needs to be corrected.

As should be appreciated, support element 110 and elastic ring 150 have to be made of physiologically and biologically compatible materials that do not cause irritation or allergic reaction when in contact with the skin. At times, these may be coated with such biocompatible material. For example, the support element, while being generally rigid, may be coated with a relatively soft layer, such as polyurethane latex, soft silicone or even fleece, to reduce friction between the foreskin and the support element.

In some embodiments, the elastic ring and/or the support element are coated or impregnated with substances having a benefit in the circumcision procedure, such as lubricants, antiseptic agents (e.g. copper based antimicrobial fibers such as those sold by Cupron, silver based products made by AcryMed), anesthetic agents, etc.

The dimensions of support element, such as support element 110 and elastic ring, such as ring 150 are selected such that once the elastic ring is mounted on the foreskin and in turn on the circumferential support 118, radial pressure is applied onto the portions of the foreskin that is held between the elastic ring and circumferential support. The pressure should be such that, on the one hand, blood flow and oxygen supply into the foreskin is obstructed thereby gradually leading to the formation of ischemic tissue, and on the other hand, the pressure does not cause significant inconvenience or pain to the subject. In some embodiments, the desired pressure is obtained by constructing an elastic ring which when in a relaxed, non-stretched state, has an inner diameter that is either equal or up to 10% lower than the outer diameter of the support element, when measured from the outer surface thereof. For example, the difference in diameters may be in the range from 1 to 10 mm, preferably from 3 to 7 mm. Such difference may cause a radial pressure of about 0.4 to 0.8 atmospheres.

The deployment element, when used, constitutes an arrangement of holders for holding the elastic ring in a stretched state thereof and for mounting the elastic ring within the circumferential support of the support element.

Figure 3:
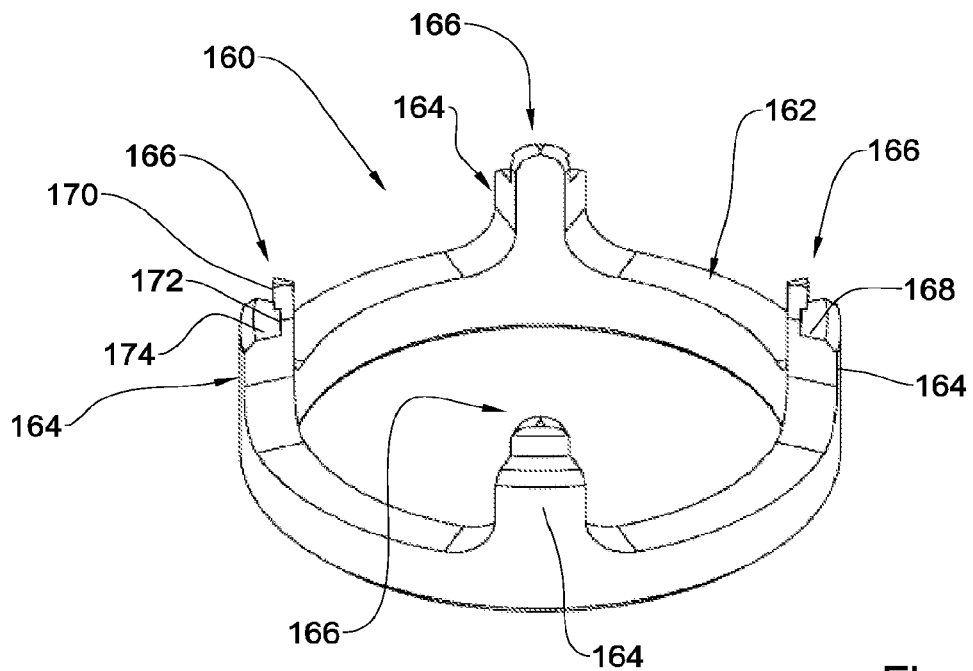
FIG. 3 shows a perspective view of a deployment device constructed and operable in accordance with an embodiment of the invention.

An exemplary structure of deployment element can be best seen in FIG. 3. According to this embodiment, deployment element 160 includes a frame 162 and an array of holders 164 (four in this specific embodiment) carried by frame 162 and projecting in a generally normal direction from the plane, defined by frame 162 dimensioned to enclose at least a part of a penis shaft. While in the exemplary embodiment illustrated in FIG. 3 the frame has a generally circular (closed ring) shape, it is to be appreciated that the frame may have an oval shape or even a polygonal shape, such as an opened square, pentagonal etc. Equally, while the frame is illustrated as a closed shape, the frame may also comprise an open segment, e.g. having a generally U shape.

Further as illustrated in FIG. 3, the arrangement is a circular array of spaced-apart holders 164. While illustrated as four substantially equally spaced apart holders (equally, at least as it is viewed by the eye), the deployment element may comprise less, e.g. three, or more than four holders.

Each holder 164 has, at its apex 166, a recess 168 for holding the elastic ring in a stretched state. Recess 168 is defined at its distal end by a low ridge 170. When referring to low, it is to be understood that the height of the ridge from a base 172 of recess 168 is at least shorter than a proximal wall 174 of the recess 168. This low ridge 170 allows securing the elastic ring in position within recess 168, on the one hand, and easy release for deployment, as will be seen below, on the other hand.

Figure 4:
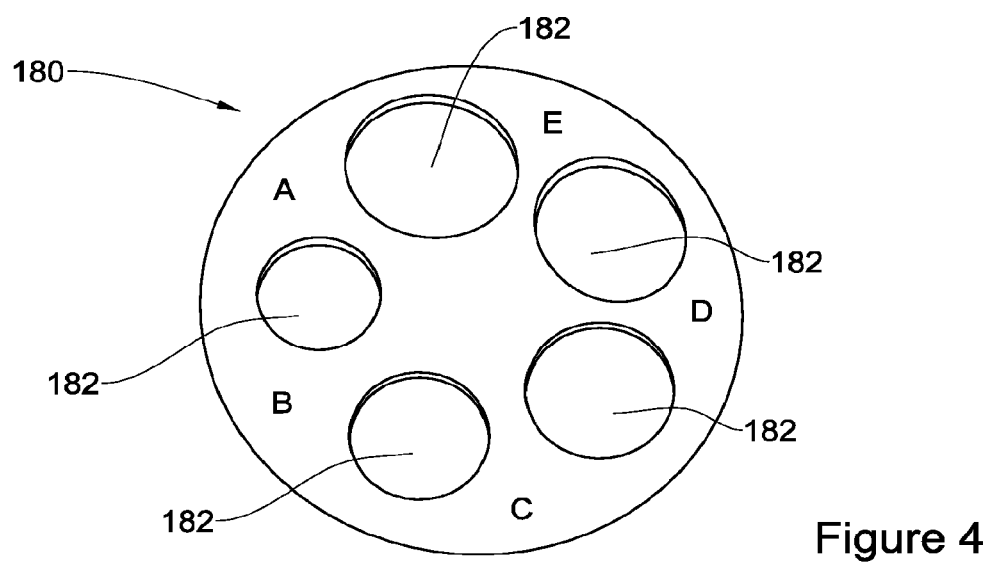
FIG. 4 shows a top view of a measuring device for measuring the diameter of a penis sulcus constructed and operable in accordance with an embodiment of the invention.

The system of the invention may also includes, by some embodiments, a penis measuring device comprising a plate with a plurality of circular openings of different diameter, each defining a penis sulcus size. In this connection, reference is made to FIG. 4 showing a penis measuring device 180 according to an embodiment of the invention.

Measuring device 180, in this specific embodiment, is in the form of a disc having five openings 182, all of a different diameter. By determining the opening that fits the penis sulcus, the diameter of the penis can be gauged and a properly dimensioned system can be selected for use in effecting necrosis of the foreskin. It is noted that the size of the support element should be such that when fitted over the sulcus it is sufficiently large to allow erection.

Reference is now made to FIGS. 5A to 5G showing steps in a deployment procedure for deploying element and elastic ring in a manner that will eventually lead to ischemic necrosis of a subject's foreskin, according to an embodiment of the invention.

Figure 5A:
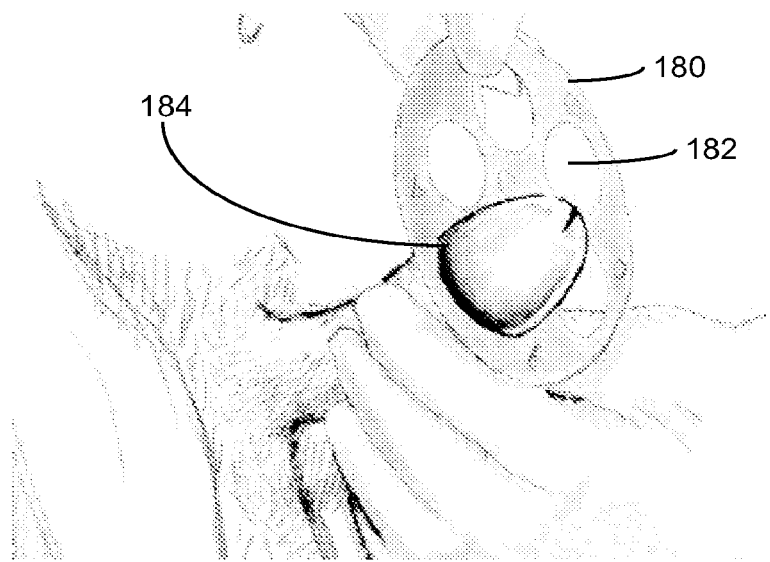
FIGS. 5A-5J show successive steps in a procedure for deploying an elastic ring over a foreskin for effecting ischemic foreskin, according to an embodiment of the invention.
Figure 5B:
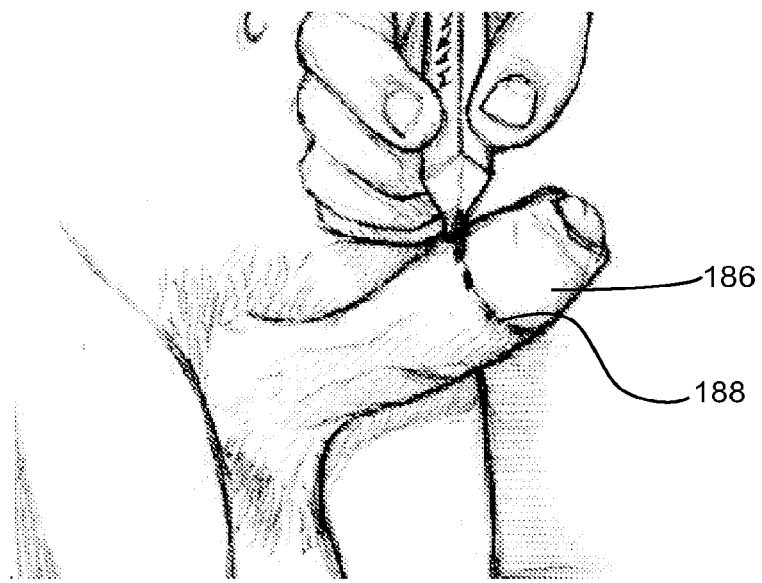

In a first step, shown in FIG. 5A, the diameter of a subject's penis, in particular, the sulcus, is gauged, using measuring device 180. In this specific case the foreskin is manually stretched backward (towards the shaft), by the practitioner or physician, to permit measurement of the penis sulcus 184 by fitting the penis in appropriate opening 182. Then, as shown in FIG. 5B, the foreskin 186 is stretched forward and a circumcision line, such as the dotted line 188 is marked over foreskin 186 according to medically acceptable standards for circumcision procedures. The circumcision line is marked with a medically acceptable marker, e.g. a non-toxic, and non-allergenic marker.

Figure 5C:
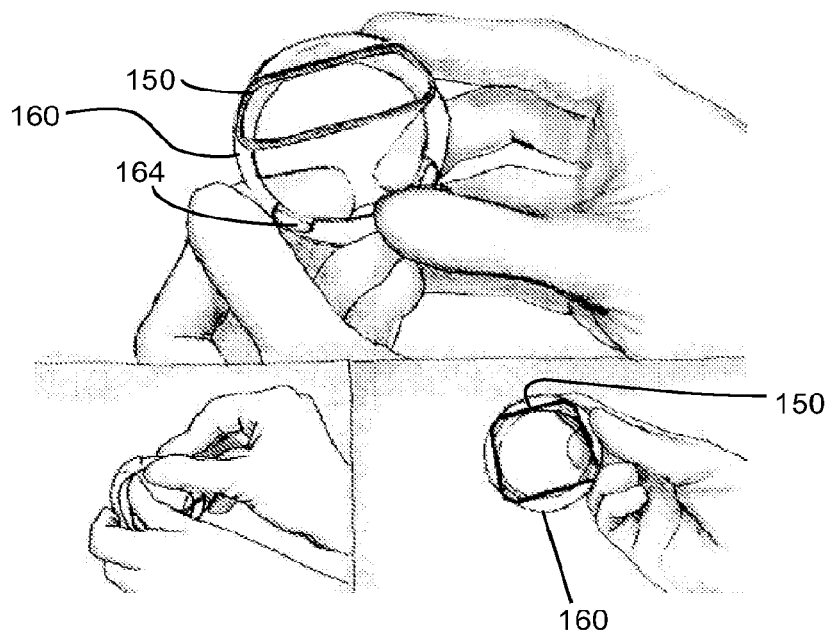
Figure 5D:
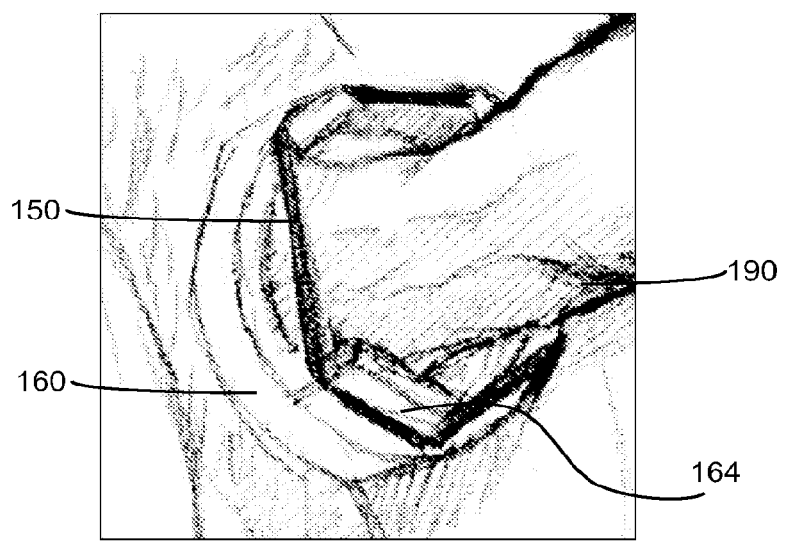

In a third step, illustrated in FIG. 5C, the elastic ring 150 is stretched over deployment element 160 and into recesses of holders 164 (in this particular example, four holders) of deployment element 160 to essentially acquire an essentially square shape. The deployment element 160 carrying the stretched elastic ring on the four holders is then passed over the penis shaft with the frame 162 of the deployment element 160 far enough along the penis shaft 190 so that foreskin 186 can be fully folded back onto the shaft 190 without touching the deployment element 160. In the particular embodiment shown in FIG. 5D, the deployment element 160 is pushed proximal to the subject's body (and the holders apex facing the glans).

Figure 5E:
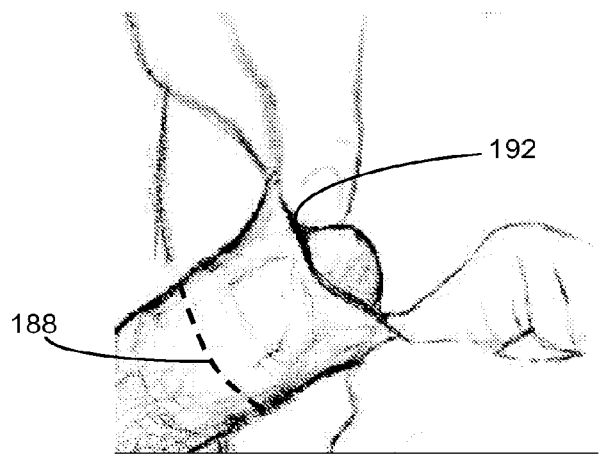
Figure 5F:
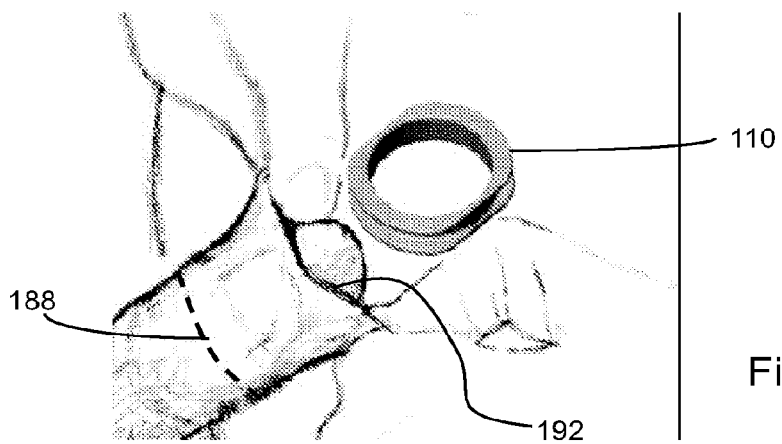

In a forth step, the foreskin is stretched forward to fully open the foreskin, as illustrated in FIG. 5E, and support element 110 is inserted via foreskin opening 192, while held stretch opened, over the penis glans (not shown), below the foreskin as sequentially shown in FIGS. 5F and 5G. The support element 110 is placed over the sulcus, such that its groove 120 is fitted below the circumcision line 188 and the two first segments are positioned at lateral sides of the penis [. The existence of the two first segments 126 and 128, where their outer surface 116 essentially tangential to the support element's inner surface 114, provides easy insertion of the support element 110 through the foreskin opening 192. Foreskin 186 may be stretched open using the hands of the physician or using various instruments such as clamps, clasps, tongs or known surgical tools (not shown).

In an alternative embodiment, the foreskin 186 may be stretched back over the shaft 190 and then support element 110 is directly placed over the glans of the penis.

In the next step, support element 110 is maneuvered around the glans of the penis until the circumferential centerline of the recess 168, (not shown) and is substantially lined up with dotted line (circumcision line) 188.

Figure 5G:
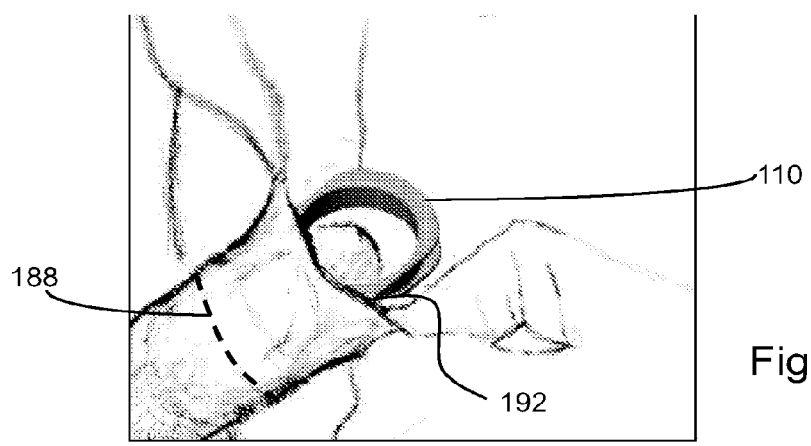
Figure 5H:
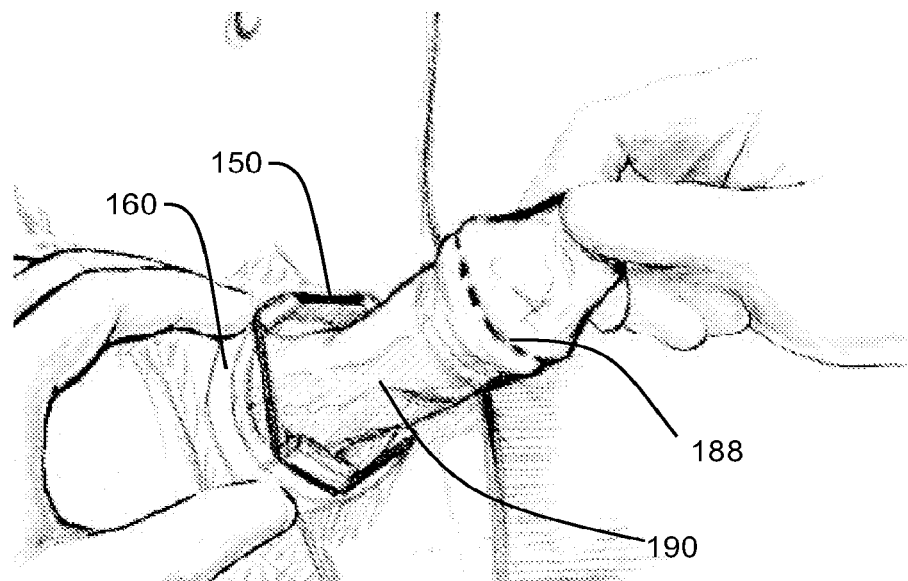
Figure 5I:
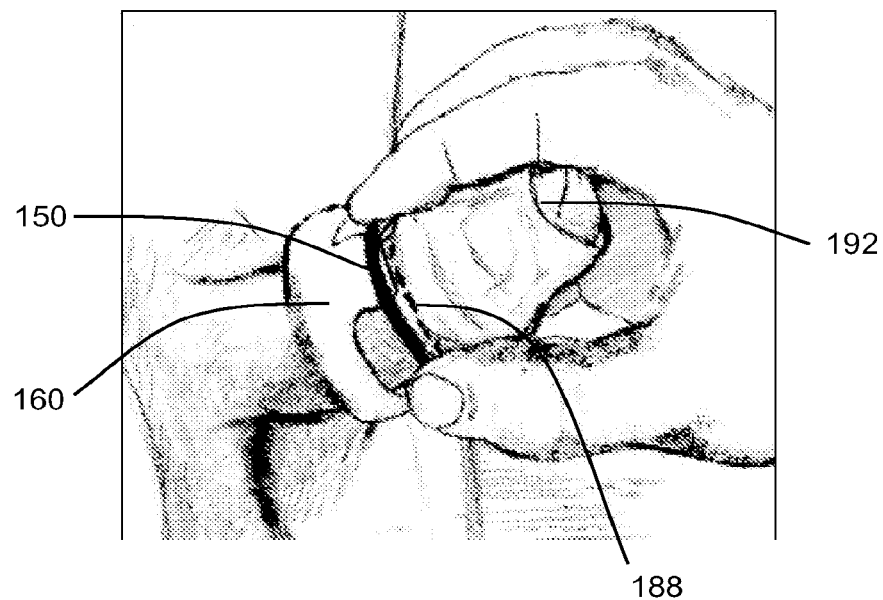

In FIGS. 5G and 5I, while holding the support element 110 in place, deployment element 160 is advanced along shaft 190 towards the glans (FIG. 5H) until elastic ring 150 lies circumferentially over circumcision line 188 and firmly grasps at least portions of circumferential recess 168 through foreskin 186 (FIG. 5I). The elastic ring 150, deployment element 160 and support element 110 are now all coupled as a fixed arrangement via inward radial compression forces applied by the elastic ring (not shown).

As shown in FIG. 5I, foreskin opening 192 no longer needs to be held stretched open. Also, it is noted that a circumferential centerline of the recess 168, does not need to necessarily line up exactly with circumcision line 188, in this step. In an alternative to this step, if foreskin 186 was pulled back along shaft 190, in this step, foreskin 186 is pulled over support element 110, either using the hands or an instrument. Support element 110 would then be maneuvered to its desired position as described above.

As illustrated, the diameter of deployment element 160 and the stretched diameter of elastic ring 150 are larger than the diameters of shaft 190 and the area of the penis around foreskin 186. In addition, at this stage, circumcision line 188 may still not lined up exactly with the circumferential centerline of the recess 168 (not shown). Thus, the fixed arrangement comprising support element 110, deployment element 160 and elastic ring 150 may be moved as a single unit distally or proximally along shaft 190 to align the centerline of recess 168 with circumcision line 188. Alternatively, foreskin 186 may be pulled in the desired direction to align the centerline of recess 186 circumcision line 188. It is noted that while the fixed arrangement of support element 110, deployment element 160 and elastic ring 150 are tightly held together, it is still possible to move the arrangement along the penis or pull the foreskin without dislodging elastic ring 150 from the deployment element 160.

Figure 5J:
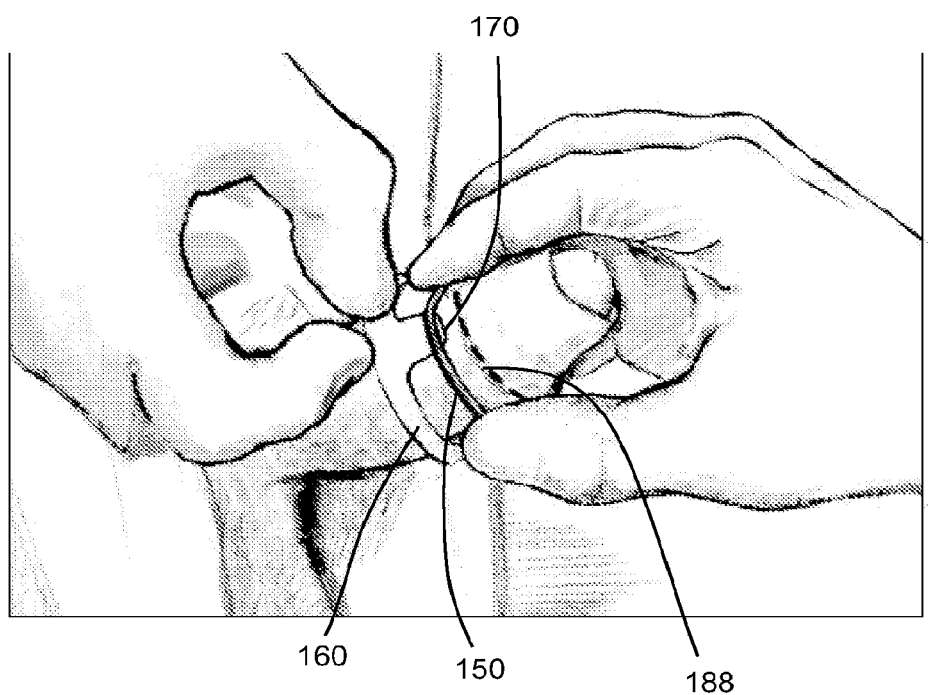

The last step of elastic ring deployment shown in FIG. 5J, where the elastic ring 150 is dislodged from each holder's ridge 170 while the support element 110 and deployment element 160 are held together in place. The stretched elastic ring is fitted over support element 110 and applies pressure on the foreskin and its support portion between support along the circumcision line 192.

Finally, once the elastic ring 150 is removed from the deployment element 160, the latter is removed from shaft 190.

At times, elastic ring may be misplaced or incorrectly placed. Therefore, to ensure that the elastic ring is correctly and circumferentially mounted over the circumcision line, the elastic ring is equipped with a safety thread (not illustrated) that allows the lifting of the elastic ring back into the deployment element recesses or adjusting the location of the ring to correctly place it over the circumcision line. Once the elastic ring is safely in place, the deployment element is removed and optionally, the safety thread is cut.

Within a period of time, typically from 72 hours to about 14 days, at times, from 5 to 10 days or from 6 to 9 days and preferably between 5 to 7 days after deployment of the elastic ring, the foreskin is necrotic and dry and this necrotic skin is (excised) removed from the penis.

Figure 6A:
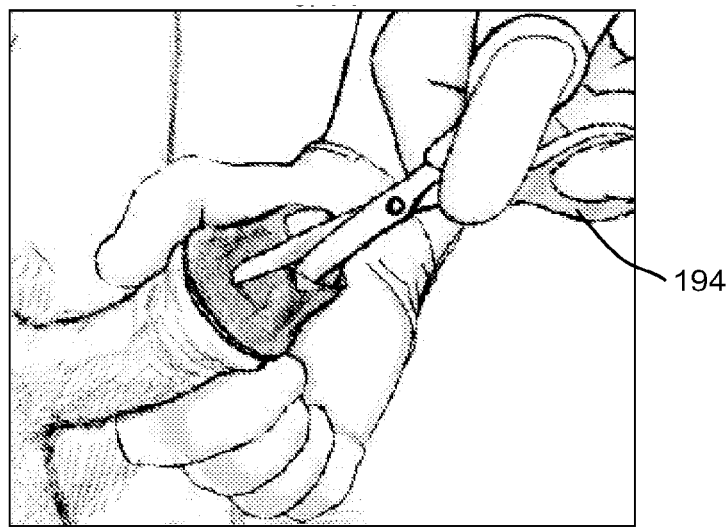
FIGS. 6A-6G show successive steps in a procedure for releasing an elastic ring from a necrotic foreskin, according to an embodiment of the invention.
Figure 6B:
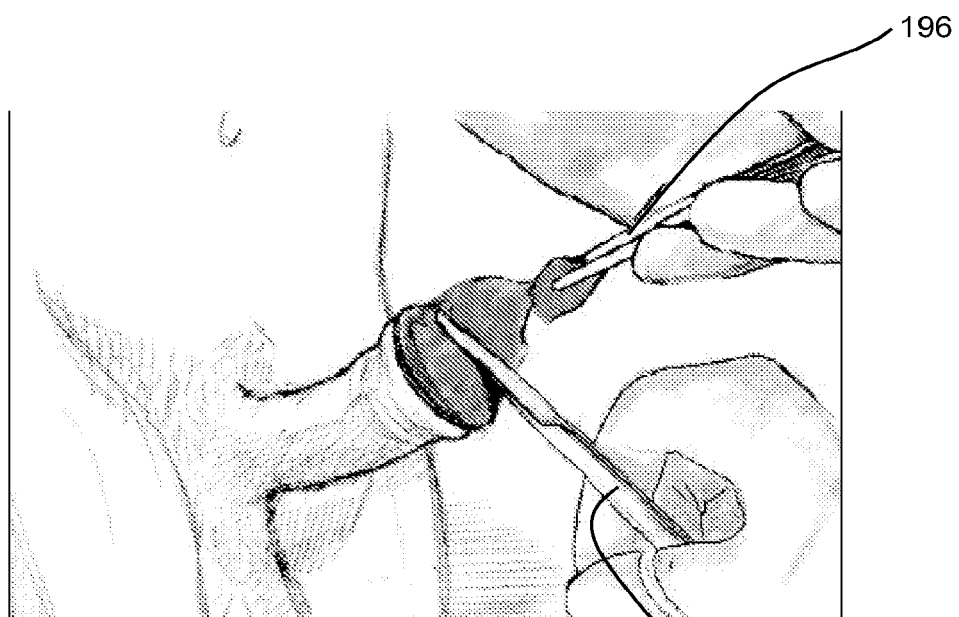

Steps for the removal of necrotic foreskin and the system according to the invention from the penis is illustrated in FIGS. 6A to 6G. Firstly, as shown in FIG. 6A, necrotic foreskin is removed by any conventional cutting tool such as scissors 194, including, without being limited thereto, scissors, razor blade, scalpel. At times, forceps 196 may be used, as illustrated in FIG. 6B. Needless to note that cutting of the necrotic foreskin is to be made as close as possible to the elastic ring. At times, dead foreskin naturally falls.

Figure 6C:
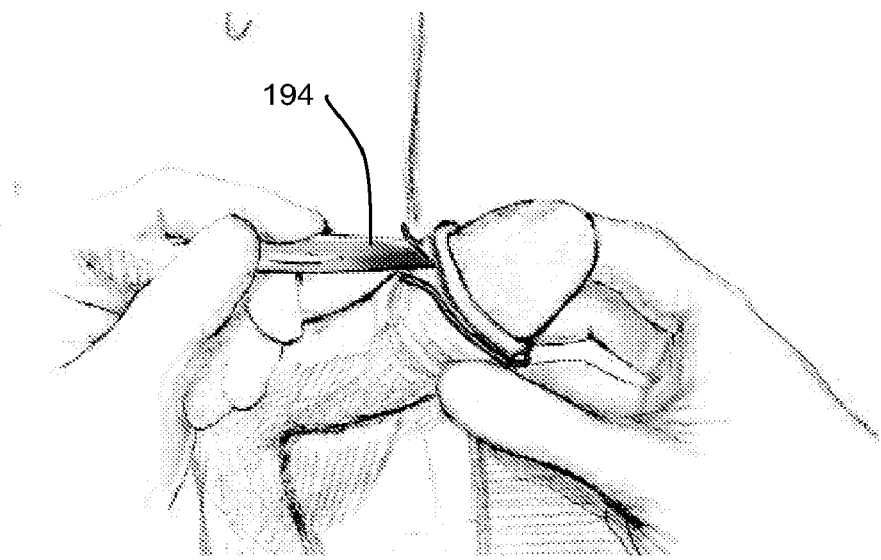
Figure 6D:
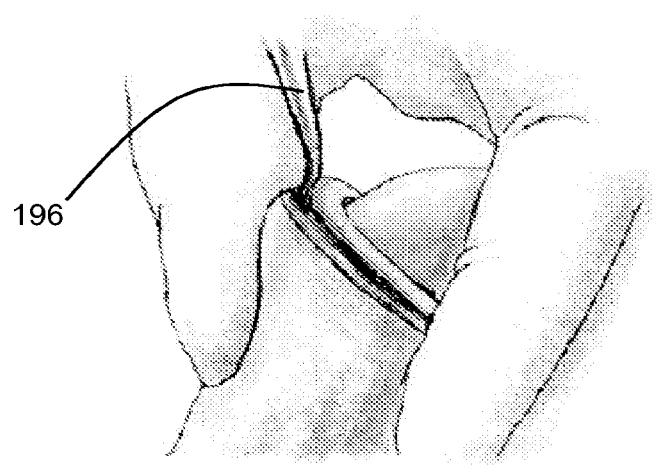
Figure 6E:
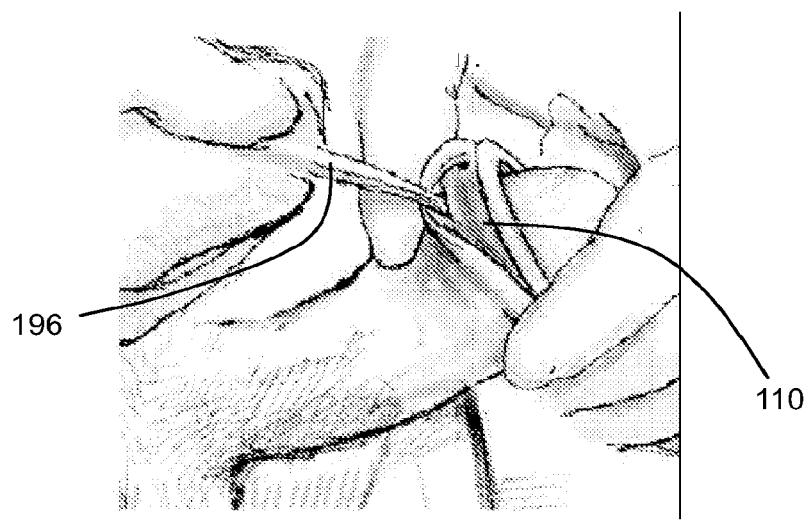
Figure 6F:
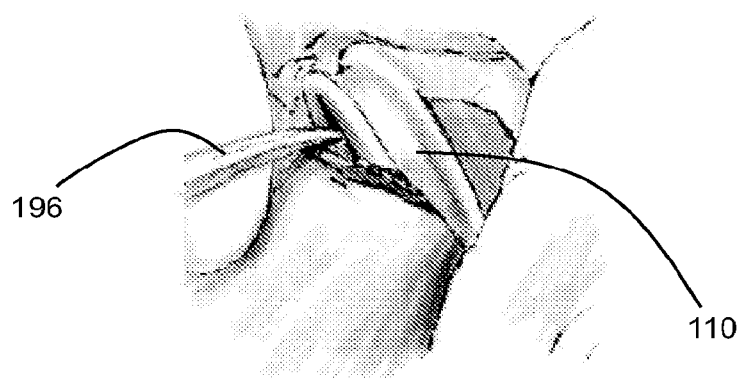
Figure 6G:
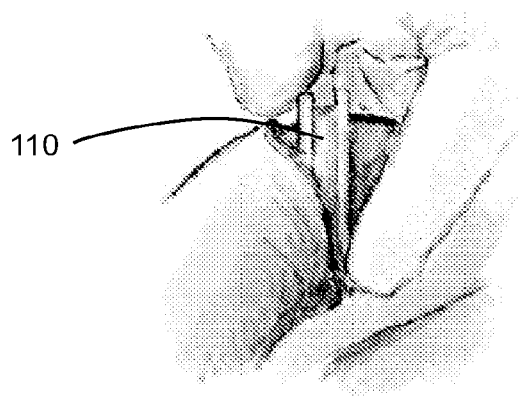

For releasing elastic ring 160 and support element 110, location of the first segments of support element (the 'flat', zero curvature segment) is verified (these first segments are to be on the lateral sides of the penis) and a cutting element is inserted between circumferential recess 168 and elastic ring 150 at one of the first segments, thereby cutting elastic ring 150, as shown in FIG. 6C.

As a last stage, the support element is released, either with a physician's fingers or using forceps 196, as clearly illustrated in FIGS. 6D to 6G.

It should be noted that by virtue of the existence of the first segments, the ring is accessible for cutting at the first segments (with flat outer surfaces), as can be seen in FIG. 6C, and is less accessible in flanking segments where it is tightly received within the deep groove of the support element. This configuration also allows cutting of the necrotic foreskin substantially adjacent to the circumferential recess 168 and the elastic ring 150 and thus eases removal of the support element 110 from the penis and reduces any pain that the subject may feel when the support element 110 is removed. In this connection, it is noted that dead skin tissue is hard and not stretchable like live skin tissue, therefore when the support element is removed from the penis (after the foreskin is removed), any dead skin tissue still coupled to the penis may cause sensations of pain as the support element is removed, since the live skin tissue adjacent to the dead skin tissue may have to stretch beyond its normal amount as the support element is removed. The existence of the two first segments substantially enables a cutting instrument to cut the foreskin substantially close to the capturing ring, thereby minimizing the amount of dead foreskin left on the penis and easing the removal of the support element. In addition, the configuration of the two parallel first segments also reduces the likelihood of the foreskin adhering to the surface of the support element as it dries, thereby also easing the removal of the support element.

The invention claimed is:

1. System for effecting ischemic necrosis in a foreskin of a penis, comprising:
   an outer elastic o-ring made from an elastic material,
   wherein the o-ring is a stretchable ring with its diameter being increased upon stretching and returning to the diameter before stretching when released from said stretching;
   a rigid inner support element defining a closed loop defining an opening dimensioned to permit a penis to pass therethrough and having an inner surface and an outer surface; the outer surface comprising a circumferential support for the elastic o-ring to be mounted thereon, said support being formed within a groove in at least part of the outer surface; at least one first segment of the outer surface having a curvature that is substantially zero, and wherein the substantially zero outer curvature of the first segment is configured so as to be manually inserted over, and removed from the penis; and
   a deployment element defining a closed loop frame with an opening and an arrangement of holders for holding the elastic o-ring in a stretched state thereof and for mounting the elastic o-ring within the circumferential support of the support element,
   wherein the elastic o-ring is configured to apply radial pressure when in stretched form.

2. The system of claim 1, wherein the outer surface of the support element is defined by a top of side walls along the groove.

3. The system of claim 1, wherein the outer surface of the support element of the first segment is substantially zero.

4. The system of claim 1, wherein said groove extends along said first segment.

5. The system of claim 1, comprising at least two of the first segments.

6. The system of claim 5, comprising two of said first segments at opposite sides of the support element.

7. The system of claim 1, wherein said arrangement comprises a circular array of spaced-apart holders.

8. The system of claim 1, wherein said arrangement comprises four holders substantially equally spaced apart.

9. The system of claim 1, wherein the frame member of said deployment element defining a closed loop frame with an opening and an arrangement of holders for holding the elastic o-ring in a stretched state thereof and for mounting the elastic ring within the circumferential support of the support element is dimensioned to enclose at least a part of the penis shaft.

10. The system of claim 9, wherein said frame member is selected from the group consisting of a closed loop member and a ring like element.

11. The system of claim 10, wherein said holders project from the frame member in a direction generally normal to a plane defined by the frame member.

12. The system of claim 11, wherein a distal end of each of the holders has a recess for holding the elastic o-ring.

13. The system of claim 1, further comprising at least one of (i) a safety thread secured to said elastic ring and (ii) a penis measuring device comprising a plate with a plurality of circular openings of different diameter, each diameter defining a penis sulcus size.

* * * * *